United States Patent [19]

Myers et al.

[11] 4,039,604

[45] Aug. 2, 1977

[54] HYDROCARBON ISOMERIZATION WITH INCREASED TEMPERATURE AND LOWERED HYDROGEN/HYDROCARBON RATIO

[75] Inventors: John W. Myers; James W. Garner, both of Bartlesville, Okla.

[73] Assignee: Phillips Petroleum Company, Bartlesville, Okla.

[21] Appl. No.: 605,710

[22] Filed: Aug. 18, 1975

[51] Int. Cl.$^2$ .................................................. C07C 5/30
[52] U.S. Cl. .......................... 260/683.68; 260/666 P; 260/683.65; 260/668 A
[58] Field of Search ...................... 260/683.68, 683.65, 260/666 P, 668 A

[56] References Cited

U.S. PATENT DOCUMENTS

| 2,831,908 | 4/1958 | Starnes et al. | 260/683.65 |
| 2,952,715 | 9/1960 | Donaldson et al. | 260/683.68 |
| 2,993,938 | 7/1961 | Bloch et al. | 260/683.68 |
| 3,449,264 | 6/1969 | Myers | 260/683.68 |

*Primary Examiner*—George Crasanakis

[57] ABSTRACT

In a process for isomerizing light hydrocarbons with a catalyst system comprising a halogenated alumina or platinum alumina when hydrogen is utilized to sustain the catalyst activity, the ratio of hydrogen to hydrocarbon in the feed is decreased and the temperature increased after a substantial period of operation. This results in an improved conversion and selectivity which allows for increasing the total catalyst life.

9 Claims, No Drawings

HYDROCARBON ISOMERIZATION WITH INCREASED TEMPERATURE AND LOWERED HYDROGEN/HYDROCARBON RATIO

BACKGROUND OF THE INVENTION

This invention relates to a low temperature isomerization process.

Isomerization of normal paraffins is one of several widely used refining processes for upgrading low value, low octane hydrocarbons to higher value, higher octane hydrocarbons for use in motor fuels and other applications. Isomerization of light normal paraffins, especially those with 4-7 carbon atoms, has become especially attractive in recent years with the development of chloride- or bromide-activated alumina or platinum alumina catalysts which have much greater activity than the older catalysts. This improvement has permitted operation at low temperatures, for instance less than 400° F (204° C) where the thermodynamic equilibrium is more favorable for the isoparaffins and has made possible both high conversion and high selectivity for the desired reactions.

As is the case with most catalytic reactions, over a period of time the activity of the catalyst declines. In this instance the decline is due to the poisoning effects of trace feed contaminants such as sulfur compounds and water and to the production of a small amount of coke which tends to obscure the catalyst surface. It is normal practice to operate two catalyst beds in series so that the first bed picks up most of the catalyst poisons and suffers the greatest decline in activity. It is also normal to practice to offset this gradual activity decline by gradually raising reactor temperature. This procedure raises catalyst activity and feed conversion while decreasing selectivity and increasing the production of coke.

The isomerization process is generally carried out in the presence of hydrogen, with hydrogen/hydrocarbon feed molal rations of 0.25:1 to 10:1 generally being preferred. The use of hydrogen has generally been found helpful in sustaining catalyst activity and in retarding cracking reactions and the production of coke.

SUMMARY OF THE INVENTION

It is an object of this invention to extend catalyst life in an isomerization process; and it is a further object of this invention to improve selectivity over the life of a catalyst.

In accordance with this information the ratio of hydrogen to hydrocarbon in an isomerization process is decreased and the temperature increased after the process has been conducted for an extended period of time.

DESCRIPTION OF THE PREFERRED EMBODIMENTS

One non-limiting example of a catalyst and process conditions to which this invention applies are disclosed in Myers U.S. Pat. No. 3,449,264 issued June 10, 1969, the disclosure of which is hereby incorporated by reference.

Briefly, the catalysts are activated by heating active alumina, platinum metal-alumina, or platinum metal-halogen-alumina at a temperature of 400° to 1500° F (204° to 816° C), preferably 1050° F to 1400° F (566° to 760° C), for a period of at least 10 minutes and up to 100 hours or more, preferably ½ to 6 hours, at least 10 minutes, preferably κ hour of heating being in the range of 900°-1500° F (482°-816° C) and at least 10 minutes, preferably ½ hour being in contact with a treating agent selected from the group consisting of Cl, HCl, Br, HBr, and Cl and Br derivatives of methane.

The isomerizable hydrocarbons to which the process of this invention is applicable include aromatics, acyclic paraffins, and naphthenes. The process is particularly suitable for the isomerization of straight chain paraffins containing 4 or more carbon atoms per molecule including n-butane, n-pentane, n-heptane and the like. Those containing 4-7 carbon atoms are preferred.

Hydrogen is introduced along with the feed initially in a concentration within the range of 0.25:1 to 10:1 moles of hydrogen per mole of feed. As catalyst activity deteriorates to the point that it becomes desirable to increase reactor temperature to maintain activity the hydrogen/hydrocarbon ratio is reduced. A procedure of stepwise increases in reactor temperature and decreases in hydrogen/hydrocarbon ratio may be advantageously continued throughout the balance of the catalyst life. The benefits of the procedure are improved conversion and selectivity performance and increased catalyst life. The ratio of hydrogen/hydrocarbon is ultimately reduced to a level within the range of 0.01:1 to 0.20:1, preferably 0.05 to 0.20 moles of hydrogen per mole of hydrocarbon. In all instances the amount of hydrogen per unit of feed will be reduced at least 20 per cent.

This increase in the temperature and decrease in the hydrogen/hydrocarbon ratio as noted hereinabove is begun when the catalyst begins to deteriorate. Generally this will be after an extended period of operation, frequently a period of one month or more, generally one month to two years or more. The increase in temperature and decrease in hydrogen/hydrocarbon ratio may then be continued for an indefinite period until a practical upper limit on the temperature is reached. This upper limit may be in the neighborhood of 650° F (343° C) although generally it will be in the range of 350° to 450° F (177° to 232° C). This gradual increase in temperature and decrease in hydrogen/hydrocarbon ratio can take place over an additional period of one month or more, generally one month to two years or more. In some instances it may be preferred to defer the stepwise reduction of hydrogen/hydrocarbon ratio until such time as the reactor temperature approaches the practical upper limit. Specifically for butane isomerization an upper limit of 425° to 450° F (218° to 232° C) has been found the maximum temperature at which best results can be obtained. At this point the hydrogen/hydrocarbon ratio is then decreased in the same manner as heretofore described.

Yet another manner for obtaining the benefits of the invention is to decrease the hydrogen/hydrocarbon ratio in lieu of raising reactor temperature, thus delaying the time for reactor temperature increases which unfavorably affect the thermodynamic equilibrium for the isoparaffins. In such embodiments the isomerization reaction is continued at a reduced ratio for a time equal to about 10 to 100 percent of the time used with the original hydrogen/hydrocarbon ratio before the temperature was increased.

The initial reactor temperature is generally below 400° F (204° C). Preferably it is in the range of 200° to 390° F (149° to 199° C) and is raised about 50-200° F (28-111° C) above the initial temperature during the life of the catalyst. For butane isomerization the initial temperature is preferably within the range of 300° to 350° F (149° to 177° C) and is increased to a level within the range of 425° to 450° F (218° to 232° C).

EXAMPLE

A run was made using a chlorided platinum alumina catalyst made in accordance with said U.S. Pat. No. 3,449,264 for n-butane isomerization. The reactor was operated initially at 315° F (157° C), 500 psig (3.55 MPa) and a liquid hourly space velocity of 8 throughout the run. The hydrogen/hydrocarbon ratio was decreased stepwise during the run.

| Step | A | B | C | D |
|---|---|---|---|---|
| Catalyst Age, bbl/lb (m³/kg) | 11.8 (4.15) | 15.8 (5.55) | 28.7 (10.1) | 29.7 (10.4) |
| H₂/HC Mol Ratio | 0.55 | 0.17 | 0.17 | 0.05 |
| Isobutane Ratio* | | | | |
| Feed | 2.0 | 2.0 | 2.0 | 2.0 |
| Product | 48.3 | 56.9 | 55.1 | 61.0 |

*Pounds (kilograms) of isobutane per 100 pounds (kilograms) of total butanes

It may be noted that despite the increasing catalyst age during the run that every time the hydrogen/hydrocarbon ratio was reduced an increase in isobutane ratio of the product was realized. At step C when hydrogen/hydrocarbon ratio was not reduced, the quality of the produce declined as a result of a near doubling of catalyst age. Shortly thereafter when hydrogen/hydrocarbon ratio was reduced, isobutane ratio of the product improved to its highest value in the run. Not illustrated, but well-known in the art, is that reactor temperature increases could also be used to incrementally raise catalyst activity.

EXAMPLE II

Another run similar to Example I was made utilizing a commercial chloride-activated platinum catalyst of another manufacturer which is widely employed for butane isomerization. Again, reactor conditions of 315° F (157° C), 500 psig (3.55 MPa) and 8 liquid hourly space velocity were maintained.

| Step | A | B | C | D |
|---|---|---|---|---|
| Catalyst Age, bbl/lb | 14.9 (5.23) | 21.4 (7.51) | 39.1 (13.7) | 40.5 (14.2) |
| H₂HC Mol Ratio | 0.55 | 0.17 | 0.17 | 0.05 |
| Isobutane Ratio | | | | |
| Feed | 2.0 | 2.0 | 2.0 | 2.0 |
| Product | 20.9 | 26.4 | 23.5 | 30.1 |

It may be observed that although the overall activity level of the catalyst was lower, the response to reductions in H₂/HC ratio was similar.

While this invention has been described in detail for the purpose of illustration it is not to be constructed as limited thereby but is intended to cover all changes and modifications within the sphere and the scope thereof.

That which is claimed is:

1. In an isomerization process wherein a hydrocarbon feed is contacted with a chloride- or bromide-activated alumina or platinum-alumina catalyst in the presence of hydrogen at a mole ratio of said hydrogen to said hydrocarbon within the range of 0.25:1 to 10:1 at a temperature below 400° F (204° C) and an isomerized product recovered, the improvement comprising: after said process has been carried out for at least 1 month increasing the temperature 50°-200° F. (58°-111° C.) and decreasing said ratio of hydrogen to hydrocarbon at least 20 percent, said decrease in said ratio of hydrogen to hydrocarbon thereby enhancing the production of the desired isomer.

2. A process according to claim 1 wherein said extended period of time in which the said process is carried out prior to said decrease in said ratio of hydrogen to hydrocarbon is within the range of one month to two years.

3. A process according to claim 1 wherein said ratio of hydrogen to hydrocarbon is reduced to 0.01:1 to 0.20:1 moles of hydrogen per mole of hydrocarbon.

4. A process according to calim 1 wherein said temperature is increased first and thereafter said ratio of hydrogen to hydrocarbon is decreased.

5. A process according to claim 1 wherein said ratio of hydrogen to hydrocarbon is decreased and thereafter said temperature is increased.

6. A process according to claim 1 wherein said ratio of hydrogen to hydrocarbon is decreased and said temperature increased simultaneously.

7. A process according to claim 1 wherein said catalyst is a chloride-activated platinum-alumina.

8. A process according to claim 7 wherein said hydrocarbon is butane and said temperature is initially within the range of 300° to 350° F and is raised to a level within the range 425° to 450° F.

9. A process according to claim 1 wherein said temperature initially is within the range of 200° to 390° F and increased 50°-200° F during the life of the catalyst.

* * * * *